United States Patent
Inoo et al.

(10) Patent No.: US 10,022,336 B2
(45) Date of Patent: Jul. 17, 2018

(54) ROPINIROLE-CONTAINING ADHESIVE PATCH

(71) Applicant: Teikoku Seiyaku Co., Ltd., Higashikagawa-shi, Kagawa (JP)

(72) Inventors: Katsuyuki Inoo, Higashikagawa (JP); Akiko Katayama, Higashikagawa (JP); Daiki Takano, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 14/647,725

(22) PCT Filed: Nov. 28, 2013

(86) PCT No.: PCT/JP2013/082055
§ 371 (c)(1),
(2) Date: May 27, 2015

(87) PCT Pub. No.: WO2014/084311
PCT Pub. Date: Jun. 5, 2014

(65) Prior Publication Data
US 2015/0297532 A1 Oct. 22, 2015

(30) Foreign Application Priority Data
Nov. 30, 2012 (JP) .................. 2012-262143

(51) Int. Cl.
*A61K 9/70* (2006.01)
*A61K 31/4045* (2006.01)
*A61K 47/06* (2006.01)

(52) U.S. Cl.
CPC .......... *A61K 9/7076* (2013.01); *A61K 9/7053* (2013.01); *A61K 9/7061* (2013.01); *A61K 31/4045* (2013.01); *A61K 47/06* (2013.01)

(58) Field of Classification Search
None
See application file for complete search history.

(56) References Cited

U.S. PATENT DOCUMENTS

| 5,807,570 A | 9/1998 | Chen et al. |
| 2008/0004329 A1* | 1/2008 | Jamieson ............. A61K 9/0014 514/418 |
| 2011/0195109 A1* | 8/2011 | Michinaka ........... A61K 9/7053 424/448 |
| 2012/0052113 A1 | 3/2012 | Uchida et al. |
| 2012/0090275 A1* | 4/2012 | Uchida ................ A61K 9/7076 53/473 |
| 2014/0112974 A1 | 4/2014 | Takagi et al. |
| 2014/0170205 A1 | 6/2014 | Uchida et al. |
| 2014/0343115 A1 | 11/2014 | Inoo et al. |

FOREIGN PATENT DOCUMENTS

| JP | 11-506462 A | 6/1999 |
| JP | 2001-518058 A | 10/2001 |
| JP | 2010-280634 A | 12/2010 |
| WO | WO 2009/107478 A1 | 9/2009 |
| WO | WO 2010/134433 A1 | 11/2010 |
| WO | WO 2012/165253 A1 | 12/2012 |
| WO | WO 2012/165254 A1 | 12/2012 |
| WO | WO 2013/081102 A1 | 6/2013 |

OTHER PUBLICATIONS

International Search Report (PCT/ISA/220 and PCT/ISA/210) dated Jan. 21, 2014 with English translation (seven pages).
Japanese-language Written Opinion (PCT/ISA/237) dated Jan. 21, 2014 (five pages).

* cited by examiner

*Primary Examiner* — Susan T Tran
(74) *Attorney, Agent, or Firm* — Crowell & Moring LLP

(57) ABSTRACT

A patch containing free ropinirole (ropinirole in free form) in an adhesive base is provided, in which the patch exhibits favorable and continuous transdermal absorbability, high drug stability, and excellent adhesiveness. A transdermal absorption patch includes free ropinirole added to an adhesive base that contains a styrene-isoprene-styrene block copolymer (SIS), one or two or more tackifier resins containing a rosin-based resin, and a softener. The transdermal absorption patch is characterized in that the compounding ratio of the rosin-based resin to the free ropinirole represented as the ratio of the weight of the combined rosin-based resin to the free ropinirole is 3.5 to 8.0. In particular, a ropinirole-containing patch wherein the rosin-based resin is a hydrogenated rosin glycerol ester and the softener is liquid paraffin is provided.

4 Claims, No Drawings

ROPINIROLE-CONTAINING ADHESIVE PATCH

TECHNICAL FIELD

The present invention relates to a patch in which free ropinirole is added to an adhesive base that contains a styrene-isoprene-styrene block copolymer (hereinafter referred to as SIS), a tackifier resin containing a rosin-based resin, and a softener.

BACKGROUND ART

Ropinirole was developed as a dopamine agonist and is used for treatment of Parkinson's disease, and oral preparations of ropinirole are distributed in the market. There have been attempts to formulate ropinirole into patches (Patent Document 1 and 2).

One advantage of the patches is that the preparations can be easily removed when a side effect occurs.

At present, ropinirole distributed in the market is its acid addition salt (specifically, ropinirole hydrochloride) because of its stability and handleability, and it is contemplated that transdermal absorption preparations are produced using the acid addition salt of ropinirole (Patent Document 3). However, generally, a transdermal absorption preparation using a drug in the form of acid addition salt has a drawback in that transdermal absorbability is much lower than that when a free drug (drug in free form) is used. When a desalting agent is used to convert the acid addition salt of ropinirole to free ropinirole within the preparation, the amount of the drug contained in the adhesive base is limited, and the acid addition salt is not completely converted to free ropinirole, so that transdermal absorbability may not be increased so much or continuous transdermal absorbability may not be provided. In addition, a metal salt may precipitate in the adhesive base, causing problems such as deterioration of the physical properties of the patch and skin irritation by the metal salt.

PRIOR ART DOCUMENTS

Patent Literature

Patent Document 1: Japanese Translation of PCT International Application No. 2001-518058
Patent Document 2: Japanese Translation of PCT International Application No. Hei. 11-506462
Patent Document 3: International Publication WO2009/107478

SUMMARY OF THE INVENTION

Problems to be Solved by the Invention

In view of the foregoing problems, the present invention provides a patch containing free ropinirole (ropinirole in free form) in an adhesive base, the patch exhibiting favorable and continuous transdermal absorbability, high drug stability, and excellent adhesiveness.

Means for Solving the Problem

To solve the above problems, the present inventors have conducted extensive studies. Consequently, the present inventors considered the chemical properties of ropinirole and confirmed the following: a preparation exhibiting favorable and continuous transdermal absorbability, high stability, and excellent adhesiveness can be obtained when free ropinirole is added to an adhesive base that contains SIS, one or two or more tackifier resins containing a rosin-based resin, and a softener, with the rosin-based resin and the free ropinirole being contained in a specific compounding ratio. Thus, the present invention has been completed.

Therefore, as a basic aspect, the present invention is a transdermal absorption patch including: an adhesive base that contains SIS, one or two or more tackifier resins containing a rosin-based resin, and a softener; and free ropinirole added to the adhesive base, wherein the compounding ratio of the rosin-based resin to the free ropinirole represented as the ratio of the weight of the combined rosin-based resin to the weight of the combined free ropinirole is 3.5 to 8.0.

As a specific aspect, the present invention is a transdermal absorption patch wherein the rosin-based resin is a hydrogenated rosin glycerol ester.

As a more specific aspect, the present invention is a transdermal absorption patch wherein the softener is liquid paraffin.

As another specific aspect, the present invention is a transdermal absorption patch including: an adhesive base that contains SIS, one or two or more tackifier resins containing a rosin-based resin, and a softener; and free ropinirole added to the adhesive base, wherein the compounding ratio of the rosin-based resin to the free ropinirole represented as the ratio of the weight of the combined rosin-based resin to the weight of the combined free ropinirole is 3.5 to 8.0, and wherein a factor (C) representing the degree of growth of ropinirole crystals on the adhesive satisfies (C)≤1 when a crystal seeding method (CS method) is performed.

Regarding the CS method, see the below description.

Effects of the Invention

In the transdermal absorption patch according to the present invention, free ropinirole is added to an adhesive base that contains SIS, one or two or more tackifier resins containing a rosin-based resin as an essential ingredient, and a softener. This configuration allows complete dissolution of the free ropinirole in the adhesive base, so that the patch that has high transdermal absorbability and also exhibits excellent drug stability and adhesiveness can be obtained.

Therefore, the transdermal absorption patch provided by the present invention allows favorable transdermal absorption of free ropinirole, which is an active ingredient, from the adhesive layer, and thus, is effective for treatment of Parkinson's disease.

EMBODIMENTS FOR CARRYING OUT THE INVENTION

A basic aspect of the present invention is a transdermal absorption patch in which free ropinirole is added to a specific rubber-based adhesive base that contains SIS as a main base.

No particular limitation is imposed on the amount of free ropinirole combined to the transdermal absorption patch provided by the present invention, so long as the patch can be prepared. The amount of combined free ropinirole is preferably within the range of 3 to 30% by weight, more preferably 5 to 20% by weight, and still more preferably 5 to 15% by weight based on the weight of the entire composition of the adhesive layer.

A free ropinirole amount of less than 3% by weight leads to an insufficient transdermal absorbability. A free ropinirole amount of not less than 30% by weight does not allow complete dissolution of the drug in the patch and causes crystallization of the drug immediately after manufacturing or during storage. In addition, the cohesion of the patch is reduced, which, for example, causes an adhesive residue to form at an application site, leading to degradation of the physical properties of the patch. Furthermore, such an amount is economically disadvantageous and therefore, unfavorable.

The amount of added SIS used as the main base of the adhesive layer of the present invention relative to the entire adhesive layer is preferably 5 to 50% by weight and more preferably 10 to 30% by weight.

The tackifier resin contained in the adhesive layer of the present invention is one containing a rosin-based resin alone or one containing two or more ingredients including a rosin-based resin. The tackifier resin provides adhesiveness to skin when mixed with SIS. Among others, the rosin-based resin has an effect of dissolving free ropinirole stably in the adhesive base. It is more preferable that the tackifier resin contain the rosin-based resin alone, since free ropinirole cannot be dissolved stably in tackifier resins other than the rosin-based resin. When two or more tackifier resins including the rosin-based resin are combined, the compounding ratio between such tackifier resins and the rosin-based resin needs to be considered. In the case of the present invention, it is desirable that the compounding ratio of the rosin-based resin to the entire tackifier resins be 0.6 or more and preferably 0.8 or more.

Examples of the rosin-based resin may include a rosin ester, hydrogenated rosin, a glycerol rosin ester, a hydrogenated rosin glycerol ester, rosin acid, and polymerized rosin. The hydrogenated rosin glycerol ester is particularly preferred.

Examples of other tackifier resins may include a petroleum-based resin, such as an aliphatic saturated hydrocarbon resin, an alicyclic saturated hydrocarbon resin, and an aromatic hydrocarbon resin, a polyterpene resin, a phenol resin, a terpene phenol resin, and a xylene resin.

The tackifier resin is contained in an amount of 20 to 60% by weight. A tackifier resin amount of less than 20% by weight is unfavorable since the physical properties of the patch deteriorate. A tackifier resin amount exceeding 60% by weight is unfavorable since the adhesive power becomes excessively strong so that physical skin irritation occurs when the patch is peeled off.

The rosin-based resin therein is contained in an amount of 20 to 60% by weight relative to the weight of the entire adhesive layer. Free ropinirole cannot be dissolved stably in the adhesive with a rosin-based resin amount of less than 20% by weight, and therefore an unfavorable effect occurs, such as precipitation of crystals of free ropinirole onto the surface of the preparation. On the other hand, the solubility of free ropinirole in the adhesive becomes excessively high at a rosin-based resin amount exceeding 60% by weight, and therefore an unfavorable effect such as reduction of transdermal absorbability occurs.

Furthermore, when the balance between the solubility in the preparation and the skin permeability of free ropinirole is taken into account, it is preferable that the rosin-based resin be contained so that the compounding ratio (weight ratio) of the rosin-based resin to the free ropinirole represented as the ratio of the weight of the combined rosin-based resin to the weight of the combined free ropinirole is 3.5 to 8.0 and preferably 4.0 to 8.0.

When the amount of the combined rosin-based resin is more than eight times the amount of the combined free ropinirole, the skin permeability of the drug is reduced. When the amount of the combined rosin-based resin is less than three and a half times the amount of the combined free ropinirole, the solubility of the drug is reduced, and therefore an unfavorable effect on the physical properties of the preparation such as crystallization of the main active ingredient occurs.

The softener contained in the adhesive layer of the present invention is added to improve skin-following ability of the preparation by softening the adhesive and also to reduce physical skin irritation by adjusting the adhesive power.

Examples of the softener contained in the transdermal absorption patch of the present invention may include liquid paraffin, polybutene, polyisobutylene, and lanolin. The combined amount thereof is 5 to 55% by weight, preferably 5 to 40% by weight, and more preferably 10 to 30% by weight.

A softener amount of less than 5% by weight is unfavorable since the preparation will have poor skin-following ability and tend to peel off easily. A softener amount exceeding 55% by weight is unfavorable since the cohesion of the adhesive is reduced to cause an adhesive residue to form at an application site.

Furthermore, when the balance between the adhesive property of the patch and the solubility of ropinirole in the preparation is taken into account, it is necessary that the compounding ratio between the tackifier resin serving as a main solvent in the present invention and the softener is considered. In the present invention, when the adhesive property of the preparation and the solubility of ropinirole in the preparation are taken into account, it is preferable that the compounding ratio (weight ratio) of the tackifier resin to the softener is adjusted so that the ratio of the weight of the combined tackifier resin to the weight of the combined softener is 0.6 to 5.0 and preferably 0.6 to 3.0. When the softener amount is more than five times the tackifier resin amount, adhesiveness of the preparation deteriorates. When the amount is less than zero point six times the tackifier resin content, the adhesive property of the preparation deteriorates and also the solubility of the drug is reduced. Accordingly, an unfavorable effect on the physical properties of the preparation such as crystallization of the main active ingredient occurs.

The transdermal absorption patch of the present invention may further contain a transdermal absorption enhancer. Examples of the transdermal absorption enhancer may include methyl laurate, hexyl laurate, triethyl citrate, isopropyl myristate (hereinafter abbreviated as IPM), myristyl myristate, octyldodecyl myristate, cetyl palmitate, triacetin, cetyl lactate, lauryl lactate, methyl salicylate, glycol salicylate, ethylene glycol salicylate, diethyl sebacate, diisopropyl sebacate, medium-chain fatty acid triglyceride, lauryl alcohol, stearyl alcohol, isostearyl alcohol, myristyl alcohol, oleyl alcohol, cetanol, glycerin monocaprylate, glycerin monolaurate, glycerin monooleate, sorbitan monolaurate, sorbitan monooleate, sucrose monolaurate, polysorbate 20, propylene glycol monolaurate, polyethylene glycol monostearate, lauromacrogol, HCO-60, lauric acid diethanolamide, N-methyl-2-pyrrolidone, 1-ethyl-2-pyrrolidone, 5-methyl-2-pyrrolidone, N-octyl-2-pyrrolidone dimethyl sulfoxide, and crotamiton.

Of these, isopropyl myristate and oleyl alcohol are particularly preferred.

If necessary, the transdermal absorption patch provided by the present invention may contain liquid components such as a plasticizer and a solubilizer.

Examples of the plasticizer may include castor oil, almond oil, olive oil, camellia oil, persic oil, peanut oil, process oil, and extender oil.

Examples of the solubilizer may include: fatty acid esters such as isopropyl myristate, diethyl sebacate, diisopropyl sebacate, diisopropyl adipate, and isopropyl palmitate; and polyols such as propylene glycol, polyethylene glycol, butylene glycol, and glycerin.

Moreover, various base components used in ordinary external preparations can be used for the transdermal absorption patch of the present invention, so long as the base components have no influence on the other components.

No particular limitation is imposed on these base components, and examples thereof may include: water-soluble polymers such as polyvinylpyrrolidone, a polyvinylpyrrolidone-vinyl acetate copolymer, polyvinyl alcohol, and polyacrylic acid; cellulose derivatives such as ethyl cellulose, hydroxypropyl cellulose, and hydroxypropyl methyl cellulose; silicon compounds such as silicic acid anhydride and light anhydride silicic acid; and inorganic fillers such as zinc oxide, aluminum oxide, titanium dioxide, silica, magnesium oxide, iron oxide, and stearic acid.

Moreover, a preservative, a refrigerant, an antimicrobial, a flavoring agent, a colorant, etc. may be added as needed.

No particular limitation is imposed on the backing for the transdermal absorption patch provided by the present invention, and any of stretchable and non-stretchable backing may be used.

More specifically, the backing used may be any of paper materials and films, sheets, laminate of these, porous membranes, foamed materials, woven fabrics, and nonwoven fabrics formed from synthetic resins such as polyethylene terephthalate, polyethylene, polypropylene, polybutadiene, an ethylene-vinyl acetate copolymer, polyvinyl chloride, polyester, nylon, and polyurethane.

A release liner formed of, for example, polyethylene terephthalate, polypropylene, or paper may be used, and polyethylene terephthalate is particularly preferred.

If necessary, the release liner may be subjected to silicon treatment to obtain optimal peel force.

A deoxidizer may be allowed to coexist with the transdermal absorption patch of the present invention. The deoxidizer used is preferably a deoxidizer formed from iron as a raw material or a deoxidizer formed from a nonferrous metal as a raw material. Examples of the method of allowing the deoxidizer to coexist may include a method in which the deoxidizer is directly sealed in a package bag and a method in which a package bag formed from a laminate including a deoxidizer film is used.

In the transdermal absorption patch of the present invention, the stability of ropinirole in the adhesive base can be relatively easily checked using a crystal seeding method (CS method), which is a simple method of testing stability of a drug. The CS method is a test method in which crystals of a drug are scattered on an adhesive base and the degree of growth of the crystals of the drug is observed to determine the short-term stability of the drug in the adhesive base.

For the patch of the present invention, the long-term stability of the drug in the preparation can be estimated from the results of the CS method. Specifically, when dissolution of the scattered drug into the adhesive base is found in the results of the CS method or the growth of the crystals of the scattered drug is not observed in the results, it can be judged that the possibility of crystallization of the drug even under long-term storage conditions is low. When the growth of the crystals of the drug is observed in the CS method, it is feared that crystals of the drug may precipitate in the preparation under long-term storage conditions.

More specifically, the CS method is performed in the following manner, and the stability of the crystals of the drug in the preparation is evaluated according to the evaluation criteria described later.

<Test Procedure of CS Method>

A release film of a patch is removed. Then a backing of the patch is secured to a glass slide, and this patch is used as a test specimen. Alternatively, part of the adhesive in the patch is collected, and the collected adhesive is applied to a glass slide and used as a test specimen.

Next, bulk powder of ropinirole is scattered directly on the adhesive portion of the test specimen. No particular limitation is imposed on the particle diameter of the scattered drug, but the particle diameter of the drug used is preferably 0.1 to 5,000 μm, in order to clearly observe the generation of crystals of the scattered drug.

The crystals of the drug immediately after they are scattered are observed under an electron microscope (for example, a digital microscope VHX-600 manufactured by KEYENCE), and image data inputted from the electron microscope through an image data processing unit is outputted.

Then DSB/S, i.e., the ratio of the total area of the crystals of the scattered drug (the projected area from above: DSB) per unit area (S) of the adhesive, is determined on the basis of the outputted image data.

After the test specimen is left to stand at room temperature for 3 to 10 days, the test specimen is observed under the electron microscope in the same manner as immediately after the crystals are scattered. Then DSA/S, i.e., the ratio of the total area of the crystals of the scattered drug (the projected area from above: DSA) per unit area (S) of the adhesive, is similarly determined.

A factor (C) representing the degree of growth of the crystals of the scattered drug in each test specimen is determined from the obtained values of DSB/S and DSA/S as follows.

$$(C)=(b)/(a)$$

[In the formula above, (a): the ratio of the total area of the crystals of the scattered drug (the projected area from above: DSB) scattered in a certain area (S) on the surface of the adhesive, i.e., DSB/S, immediately after the start of the test (immediately after the crystals of the drug are scattered).

(b): the ratio of the total area of the crystals of the scattered drug (the projected area from above: DSA) scattered in the certain area (S) on the surface of the adhesive, i.e., DSA/S, after completion of the test (10 days after the crystals of the drug are scattered).

<Evaluation Criteria>

Evaluation is made using the value of (C) obtained from the above formula according to the evaluation criteria below.

(i) (C)≤1:

Growth of the crystals of the drug scattered on the adhesive is not observed, or the crystals are reduced in size.

(ii) (C)>1:

The crystals of the drug scattered on the adhesive have grown.

An example of a method of producing the transdermal absorption patch provided by the present invention will next be described.

Specifically, the base ingredients including SIS, a tackifier resin, and a softener are dissolved in an organic solvent such as toluene and then are stirred and mixed with other ingredients that have been dissolved in a suitable organic solvent. The solution obtained is applied over a silicon-treated release liner and dried at 90° C. for 10 minutes to form an adhesive layer. The polyethylene terephthalate side of a backing is laminated to the adhesive layer obtained and subsequently the laminate is cut into an appropriate size and shape, whereby the transdermal absorption preparation of the present invention can be obtained.

The thickness of the adhesive layer is preferably about 30 to about 200 μm and more preferably about 50 to about 100 μm.

The thickness of less than 30 μm may cause the duration of release of the drug to become short. The thickness of more than 200 μm may increase the amount of the drug contained in the adhesive layer, and this causes an increase in production cost.

EXAMPLES

The present invention will next be more specifically described by way of Examples and Comparative Examples, but the present invention is not limited to the following Examples.

Example 1

Free ropinirole was dissolved in advance in toluene based on the composition amount (unit: % by weight) or the compounding ratio shown in Table 1 and subsequently was mixed with other ingredients that had been dissolved in toluene. The mixture was coated on a release film, then dried to remove toluene and laminated with a PET film backing to obtain the transdermal absorption preparation of the present invention.

Examples 2 to 8

Respective patches in Examples 2 to 8 having composition amounts (unit: % by weight) and the compounding ratio shown in Table 1 were obtained in accordance with the production method in Example 1.

Comparative Examples 1 to 6

Patches in respective Comparative Examples 1 to 6 were produced in the same manner as in Example 1 except that respective components were used in ratios shown in Table 2 (unit: % by weight).

TABLE 2

| | COMPARATIVE EXAMPLES | | | | | |
|---|---|---|---|---|---|---|
| | 1 | 2 | 3 | 4 | 5 | 6 |
| FREE ROPINIROLE | 5 | 5 | 5 | 5 | 10 | 10 |
| SIS | 20 | 20 | 20 | 20 | 20 | 20 |
| HYDROGENATED ROSIN GLYCEROL ESTER | 10 | 15 | 50 | 60 | 20 | 30 |
| LIQUID PARAFFIN | 65 | 60 | 25 | 15 | 50 | 40 |
| HYDROGENATED ROSIN GLYCEROL ESTER/ FREE ROPINIROLE | 2.0 | 3.0 | 10.0 | 12.0 | 2.0 | 3.0 |
| TACKIFIER RESIN/ LIQUID PARAFFIN | 0.15 | 0.25 | 2.5 | 4.0 | 0.4 | 0.75 |
| PRESENCE/ABSENCE OF PRECIPITATED CRYSTALS | X | X | ○ | ○ | X | X |
| ADHESIVENESS OF PREPARATION (ADHESIVE POWER DURING APPLICATION PERIOD) | X | X | ○ | X | X | X |
| ADHESIVENESS OF PREPARATION (PEEL FORCE) | ○ | ○ | Δ | ○ | ○ | ○ |
| FLUX (μg/cm$^2$/hr) | — | — | 7.7 | — | — | — |

Test Example 1: Examination of Stability of Drug in Preparations by Crystal Seeding Method (CS Method)

The stability of the drug in the preparations of respective Examples and Comparative Examples was examined by the CS method described above.

TABLE 1

| | EXAMPLES | | | | | | | |
|---|---|---|---|---|---|---|---|---|
| | 1 | 2 | 3 | 4 | 5 | 6 | 7 | 8 |
| FREE ROPINIROLE | 5 | 5 | 5 | 5 | 10 | 10 | 10 | 10 |
| SIS | 20 | 20 | 20 | 20 | 20 | 20 | 20 | 20 |
| HYDROGENATED ROSIN GLYCEROL ESTER | 20 | 25 | 30 | 40 | 35 | 40 | 45 | 50 |
| LIQUID PARAFFIN | 55 | 50 | 45 | 35 | 35 | 30 | 25 | 20 |
| HYDROGENATED ROSIN GLYCEROL ESTER/ FREE ROPINIROLE | 4.0 | 5.0 | 6.0 | 8.0 | 3.5 | 4.0 | 4.5 | 5.0 |
| TACKIFIER RESIN/ LIQUID PARAFFIN | 0.36 | 0.5 | 0.67 | 1.14 | 1 | 1.33 | 1.8 | 2.5 |
| PRESENCE/ABSENCE OF PRECIPITATED CRYSTALS | ○ | ○ | ○ | ○ | ○ | ○ | ○ | ○ |
| ADHESIVENESS OF PREPARATION (ADHESIVE POWER DURING APPLICATION PERIOD) | Δ | Δ | Δ | ○ | ○ | ○ | ○ | ○ |
| ADHESIVENESS OF PREPARATION (PEEL FORCE) | Δ | Δ | ○ | ○ | ○ | ○ | ○ | Δ |
| FLUX (μg/cm$^2$/hr) | 21.2 | — | 15.9 | 10.9 | 25.5 | 23.1 | 20.6 | 15.8 |

The adhesive portion in each of the Examples and Comparative Examples was collected as a test sample, and each of the test samples was adhered to a glass slide and used as a test specimen.

Observation by a microscope was performed using a digital microscope (type: KEYENCE VHX-600, magnification: 400×). The particle diameter of the used bulk powder of ropinirole scattered on the adhesive was 5 to 3,000 µm, and the test was terminated 10 days after the drug was scattered.

The results thereof are also shown in Table 1 and Table 2.

In each Table, the factor (C) representing the degree of growth of crystals is shown as circle or cross according to the following evaluation criteria.

Circle: when (C)≤1
Cross: when (C)>1

In the adhesives in respective Examples that are used as the transdermal absorption patches of the present invention, growth of the crystals was not observed, and it was found that free ropinirole was stably dissolved in the adhesive base.

However, in the preparations in Comparative Examples 1, 2, 5, and 6, growth of the crystals was found after completion of the test, and it was suggested that ropinirole was present in the adhesive base in an unstable state.

Test Example 2: Examination of Adhesiveness of Preparations

The patches of respective Examples and Comparative Examples immediately after manufacturing were applied to the lateral upper arm of volunteers with informed consent. 24 hours later, the patches were peeled off and (i) adhesiveness during the application period and (ii) peel force were examined.

The results of examination are also shown in Table 1 and Table 2.

Each of the items to be examined was evaluated on the basis of the criteria described below.
(i) Adhesive Power During Application Period
○: there is no peeling or the part peeled during the application period is 10% or less of the application area.
Δ: 10 to 30% part of the application area is peeled off and turned up during the application period.
×: the patch falls off or approximately 30% or more part of the application area is peeled off and turned up during the application period.
(ii) Peel Force
○: almost no pain is felt when the preparation is peeled off.
Δ: slight pain is felt when the preparation is peeled off.
×: strong pain is felt when the preparation is peeled off.
As a result, the preparations of respective Examples exhibited an excellent adhesive property.

Test Example 3: Skin Permeation Test on Hairless Mice (In Vitro)

The patches in Example 1, Examples 3 to 8, and Comparative Example 3 were subjected to an in vitro skin permeation test using skin excised from hairless mice (HR-1, 7 weeks old).

The back skin of a hairless mouse was removed. The dermis was set on a receptor with its inside filled with phosphate buffered saline, and warm water at 37° C. was refluxed through a water jacket.

Each test patch was punched into a circular shape (1.54 cm$^2$) and applied to the excised skin. The receptor solution was sampled at time intervals, and the skin permeation amount of the drug was measured by the high-performance liquid chromatography. The rate of transdermal absorption (Flux: µg/cm$^2$/hr) in steady state was computed from the results of the measurement.

The results are also shown in Table 1 and Table 2.

From the results shown in respective Tables, the transdermal absorption patches of respective Examples of the present invention were found to be a preparation that exhibits better transdermal absorbability as compared to the preparation of Comparative Example 3.

From the results of the above-mentioned Test Examples, the transdermal absorption patches of respective Examples of the present invention is a balanced patch excellent in all three parameters, that is, transdermal absorbability, adhesiveness, and stability, while there was no balanced preparation found that was excellent in all the above-mentioned three parameters among the preparations of Comparative Examples.

[Exemplary Preparations]

Hereinbelow, exemplary preparations other than the patches of the present invention shown in Examples 1 to 8 are shown as exemplary preparations 1 to 15 in Tables 3 to 5 below. However, the present invention is not limited thereto.

TABLE 3

| | EXEMPLARY PREPARATIONS | | | | | |
|---|---|---|---|---|---|---|
| | 1 | 2 | 3 | 4 | 5 | 6 |
| FREE ROPINIROLE | 5 | 5 | 5 | 5 | 5 | 5 |
| SIS | 20 | 20 | 20 | 20 | 20 | 20 |
| HYDROGENATED ROSIN GLYCEROL ESTER | 20 | 20 | 20 | 30 | 30 | 30 |
| ALICYCLIC SATURATED HYDROCARBON RESIN | 8 | 10 | 13 | 5 | 10 | 15 |
| LIQUID PARAFFIN | 47 | 45 | 42 | 40 | 35 | 30 |
| HYDROGENATED ROSIN GLYCEROL ESTER/ FREE ROPINIROLE | 4 | 4 | 4 | 6 | 6 | 6 |
| ENTIRE TACKIFIER RESIN/LIQUID PARAFFIN | 0.60 | 0.67 | 0.79 | 0.88 | 1.14 | 1.50 |
| HYDROGENATED ROSIN GLYCEROL ESTER/ ENTIRE TACKIFIER RESIN | 0.71 | 0.67 | 0.61 | 0.86 | 0.75 | 0.67 |

TABLE 4

| | EXEMPLARY PREPARATIONS | | | | |
|---|---|---|---|---|---|
| | 7 | 8 | 9 | 10 | 11 |
| FREE ROPINIROLE | 5 | 5 | 5 | 10 | 10 |
| SIS | 20 | 20 | 20 | 20 | 20 |
| HYDROGENATED ROSIN GLYCEROL ESTER | 30 | 40 | 40 | 35 | 35 |
| ALICYCLIC SATURATED HYDROCARBON RESIN | 20 | 10 | 16 | 10 | 17 |
| LIQUID PARAFFIN | 25 | 25 | 19 | 25 | 18 |
| HYDROGENATED ROSIN GLYCEROL ESTER/ FREE ROPINIROLE | 6 | 8 | 8 | 3.5 | 3.5 |
| ENTIRE TACKIFIER RESIN/ LIQUID PARAFFIN | 2.00 | 2.00 | 2.95 | 1.80 | 2.89 |
| HYDROGENATED ROSIN GLYCEROL ESTER/ENTIRE TACKIFIER RESIN | 0.60 | 0.80 | 0.71 | 0.78 | 0.67 |

TABLE 5

| | EXEMPLARY PREPARATIONS | | | |
|---|---|---|---|---|
| | 12 | 13 | 14 | 15 |
| FREE ROPINIROLE | 5 | 5 | 10 | 10 |
| SIS | 15 | 25 | 15 | 25 |
| HYDROGENATED ROSIN GLYCEROL ESTER | 30 | 40 | 35 | 35 |
| ALICYCLIC SATURATED HYDROCARBON RESIN | 5 | 10 | 10 | 10 |
| LIQUID PARAFFIN | 45 | 20 | 30 | 20 |
| HYDROGENATED ROSIN GLYCEROL ESTER/ FREE ROPINIROLE | 6 | 8 | 3.5 | 3.5 |
| ENTIRE TACKIFIER RESIN/ LIQUID PARAFFIN | 0.78 | 2.50 | 1.50 | 2.25 |
| HYDROGENATED ROSIN GLYCEROL ESTER/ENTIRE TACKIFIER RESIN | 0.86 | 0.80 | 0.78 | 0.78 |

INDUSTRIAL APPLICABILITY

The present invention can provide a transdermal absorption preparation containing free ropinirole that has favorable transdermal absorbability, high drug stability, and excellent adhesiveness, and therefore, contributes significantly to disease treatment of Parkinson's disease.

The invention claimed is:

1. A transdermal absorption patch comprising:
an adhesive base that contains a styrene-isoprene-styrene block copolymer, one or two or more tackifier resins containing a rosin-based resin, and a softener; and
free ropinirole added to the adhesive base, wherein the rosin based resin and free ropinirole are present in the adhesive base at a compounding ratio of 3.5 to 8.0, wherein the compounding ratio of the rosin-based resin to the free ropinirole is a ratio of the weight of the combined rosin-based resin to the weight of the free ropinirole.

2. The transdermal absorption patch according to claim 1, wherein the rosin-based resin is a hydrogenated rosin glycerol ester.

3. The transdermal absorption patch according to claim 1, wherein the softener is liquid paraffin.

4. A transdermal absorption patch comprising:
an adhesive base that contains a styrene-isoprene-styrene block copolymer, one or two or more tackifier resins containing a rosin-based resin, and a softener; and
free ropinirole added to the adhesive base, wherein the rosin based resin and the free ropinirole are present in the patch in amounts that provide a compounding ratio of 3.5 to 8.0, wherein the compounding ratio is the ratio of the amount by weight of the combined rosin-based resin to the amount by weight of the free ropinirole and wherein the adhesive base has a value "(C)" of ≤1 wherein (C)=(b)/(a), wherein,
(a)=a ratio of a total area of crystals of ropinirole (a DSB) scattered in a certain area (S) on a surface of the adhesive base (DSB/S), immediately after the crystals of the free ropinirole are scattered on the adhesive base, and
(b)=a ratio of the total area of the crystals of the scattered free ropinirole (the projected area from above: DSA) scattered on a certain area (S) on the surface of the adhesive (DSA/S), after completion of the test (10 days after the crystals of the free ropinirole are scattered).

* * * * *